US00PP37308P2

(12) United States Plant Patent
Vivek et al.

(10) Patent No.: US PP37,308 P2
(45) Date of Patent: Mar. 3, 2026

(54) ***PHILODENDRON* PLANT NAMED 'BVCL01'**

(50) Latin Name: *Philodendron erubescens*
Varietal Denomination: BVCL01

(71) Applicants: Eden Garden For Exotic Flora, Kanyakumari (IN); Super Nursery, Phatthana Nikhom (TH)

(72) Inventors: Bejolin Vivek, Kanyakumari (IN); Chokechai Leuangthammachad, Phatthana Nikhom (TH)

( * ) Notice: Subject to any disclaimer, the term of this patent is extended or adjusted under 35 U.S.C. 154(b) by 0 days.

(21) Appl. No.: 18/831,584

(22) Filed: May 15, 2025

(51) Int. Cl.
*A01H 5/12* (2018.01)
*A01H 6/10* (2018.01)

(52) U.S. Cl.
USPC ..... Plt./381

(58) Field of Classification Search
USPC ..... Plt./381
See application file for complete search history.

*Primary Examiner* — Susan McCormick Ewoldt
*Assistant Examiner* — Zachariah Allan Kay
(74) *Attorney, Agent, or Firm* — Samuel R. McCoy, Jr.

(57) ABSTRACT

'BVCL01' is a distinctive *Philodendron* plant which is characterized by uniquely variegated laminas with variegated foliage comprised of a light pink base coloration and irregular blotches of varying size and color, from magenta to dark pink, green to greyed-green, and brown; as well as vivid magenta petioles and petiole wings with dark pink irregular longitudinal stripes, and the stability of all characteristics from generation to generation.

3 Drawing Sheets

Latin name of the genus and species: The Latin name of the genus and species of the novel variety disclosed herein is *Philodendron erubescens.*

Variety denomination: The inventive variety of *Philodendron* disclosed herein has been given the variety denomination 'BVCL01'.

BACKGROUND OF THE INVENTION

Parentage: 'BVCL01' is a spontaneous whole-plant mutation which was first discovered in July of 2024 at a commercial greenhouse facility in Phatthana Nikhom, Thailand, growing amongst a cultivated population of *Philodendron erubescens* 'Pink Princess' plants (not patented). The mutation was first noted for its unique foliage variegation, relative to the bicolored variegation of 'Pink Princess'. Meristematic tissue was harvested from said mutation and in vitro micropropagation was first performed in October of 2024. The resulting plurality of tissue cultured plantlets produced were subsequently grown in a greenhouse for two generations to confirm the stability and relative uniformity of the unique foliage colorations. In December of 2024, the resulting plants were determined to have a stable, unique variegation pattern and were selected for further propagation. This new plant was given the name 'BVCL01'.

Asexual Reproduction: Asexual reproduction of the new cultivar 'BVCL01', by way of meristematic tissue culture micropropagation, was first initiated in 2024 in Phatthana Nikhom, Thailand. Through two subsequent generations, the unique features of this cultivar have proven to be stable and true to type.

SUMMARY OF THE INVENTION

The cultivar 'BVCL01' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'BVCL01'. These characteristics in combination distinguish 'BVCL01' as a new and distinct *Philodendron* cultivar:

1. *Philodendron* 'BVCL01' exhibits uniquely variegated laminas with a light pink base coloration and irregular blotches of varying size and color, from magenta to dark pink, green to greyed-green, and brown; and
2. *Philodendron* 'BVCL01' exhibits vivid magenta petioles and petiole wings with dark pink irregular longitudinal striation, and the stability of all characteristics from generation to generation.

BOTANICAL DESCRIPTION OF THE PLANT

Figure 1:
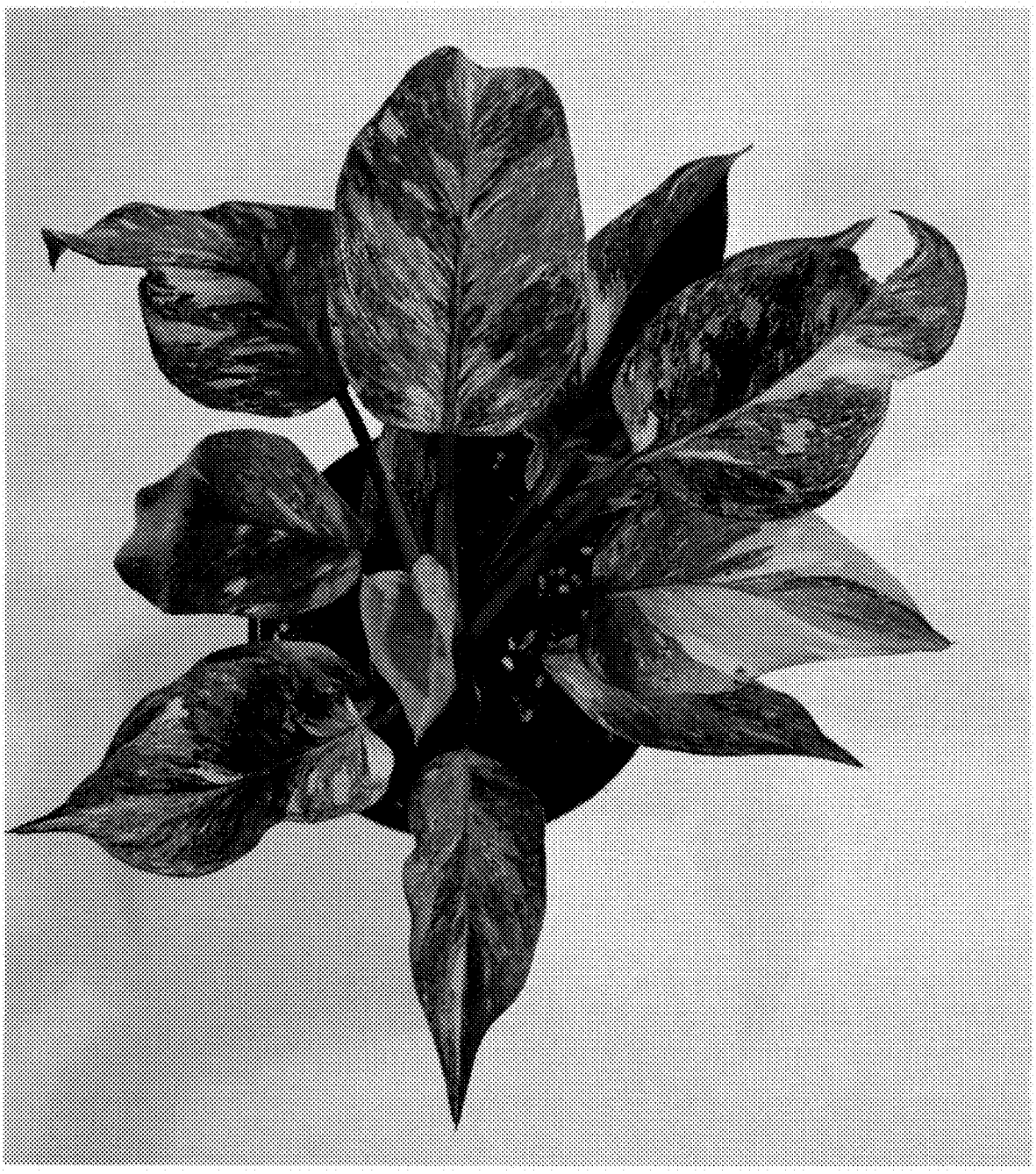
FIG. 1 illustrates, as nearly true as it is reasonably possible to make the same in color photographs of this type, an exemplary plant of 'BVCL01' grown in a commercial greenhouse in Phatthana Nikhom, Thailand. These plants are approximately 14 months old, in a 10 cm container.
Figure 2:
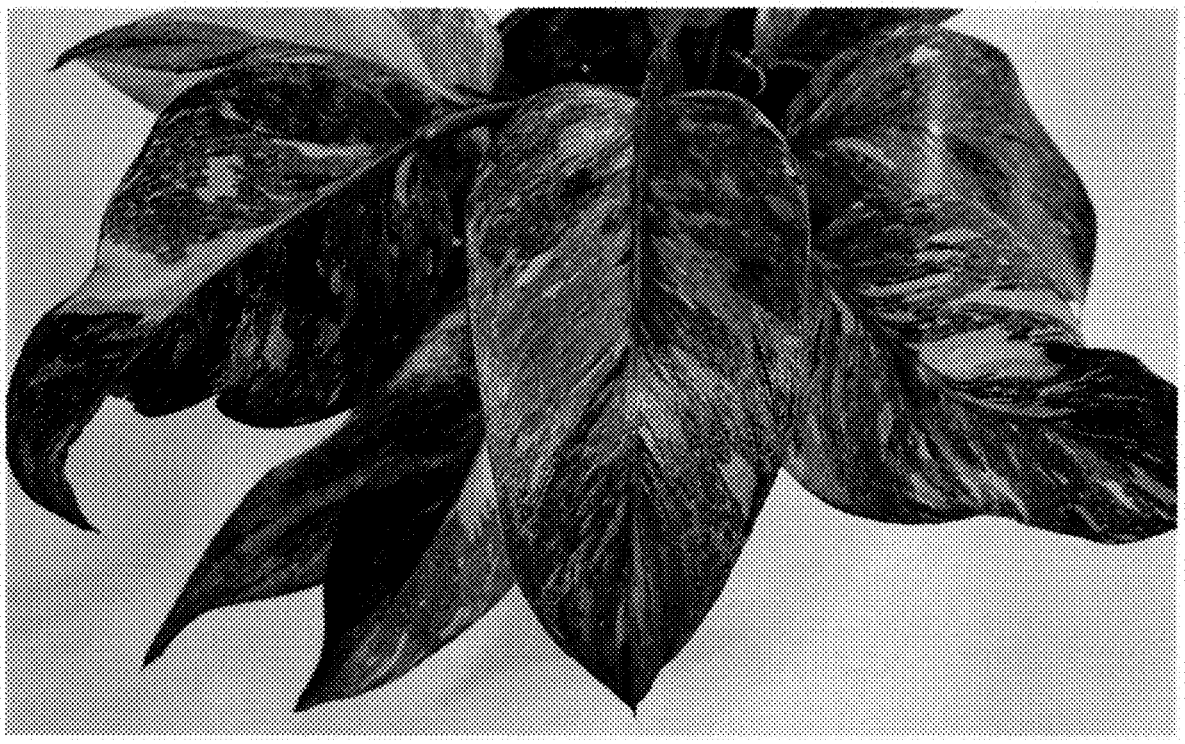
FIG. 2 illustrates, as nearly true as it is reasonably possible to make the same in color photographs of this type, the mature foliage's adaxial surface of 'BVCL01'.
Figure 3:
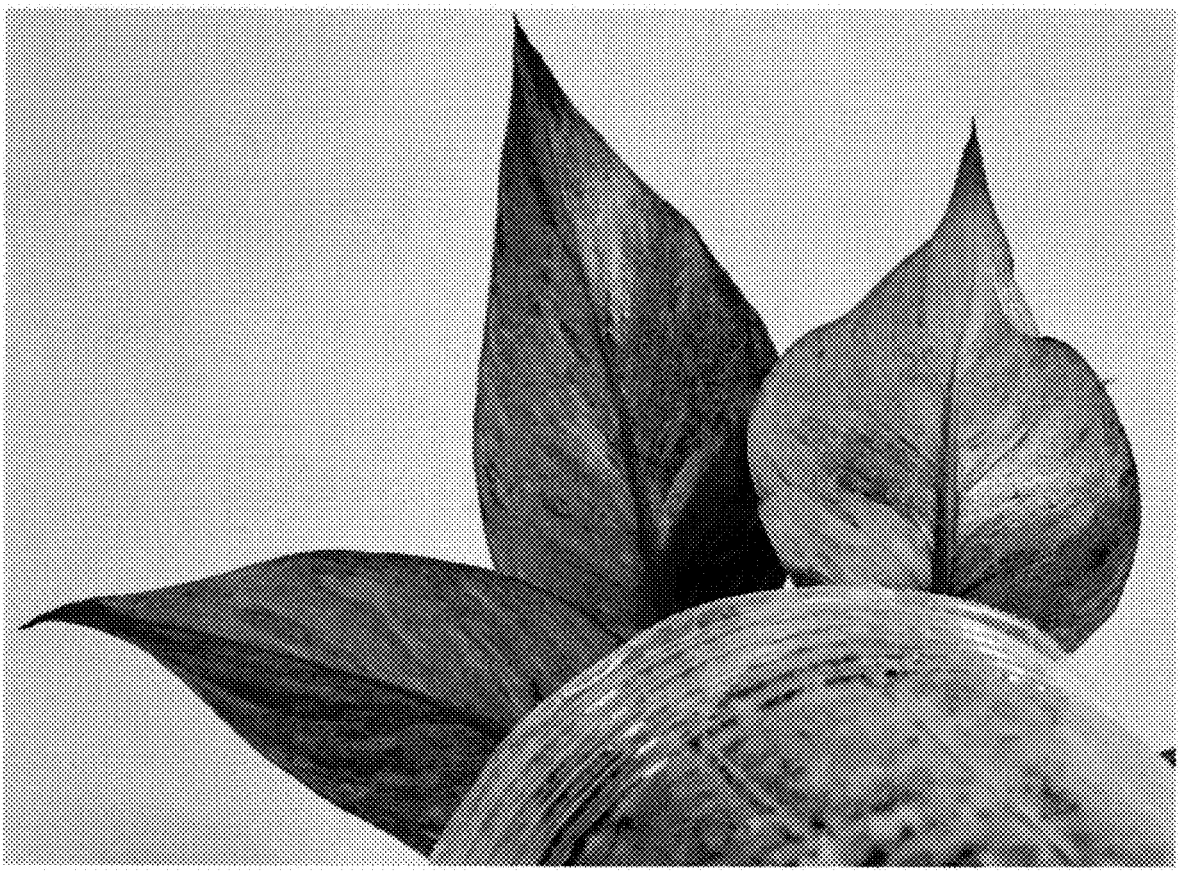
FIG. 3 illustrates, as nearly true as it is reasonably possible to make the same in color photographs of this type, the mature foliage's abaxial surface of 'BVCL01'.

The following observations and measurements, made in May of 2025, describe averages from a 14-month-old 'BVCL01' plant grown in a 10 cm nursery container at commercial greenhouse in Phatthana Nikhom, Thailand. Plants were produced using conventional greenhouse production protocols for *Philodendron* species which consisted of overhead irrigation once every two days and routine application of a granular 13-13-13. Plants were grown under shade (ranging from 5,000 to 25,000 lux) with ambient temperatures ranging from 26 to 38 degrees Celsius and humidity levels ranging from 70 to 90 percent.

Those skilled in the art will appreciate that certain characteristics will vary with older or, conversely, with younger plants. 'BVCL01' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climatic and cultural conditions. Color notations are based on *The Royal Horticultural Society Colour Chart*, The Royal Horticultural Society, London, Sixth Edition.

A botanical description of 'BVCL01' and a comparison with the parent plant and most similar commercial cultivar are provided below.

Plant description:

*Growth habit*.—Broad spreading to upright herbaceous perennial with foliage growth from basal shoots.

*Plant profile shape*.—Globular to flattened globular.

*Height*.—13.2 cm at approximately 14 months of age.

*Width*.—25 cm at approximately 14 months of age.

*Number of basal shoots per plant*.—1.

*Propagation*.—Type — Asexual propagation is accomplished by way of meristematic tissue culture micropropagation. Time to initiate roots — Approximately 4 to 6 weeks to initiate roots at an average ambient temperature of 21 degrees Celsius. Crop time — Approximately 16 to 20 weeks to produce a well-rooted, marketable 10 cm container from a rooted cutting.

*Disease and pest resistance or susceptibility*.—Neither susceptibility nor resistance to pests and diseases common to other *Philodendron* have been observed.

*Environmental tolerances*.—Adapt to temperatures as low as 5 degrees Celsius and at least as high as 40 degrees Celsius.

Roots:

*Density*.—Not very dense.

*Texture*.—Fleshy, non-fibrous.

*Color*.—Brown, nearest to RHS 200A.

Foliage:

*Quantity*.—12 leaves per shoot.

*Arrangement*.—Alternate whorl.

*Attachment*.—Petiolate.

*Division*.—Simple.

*Lamina*.—Shape — Ovate to near-cordate. Length — 12.5 cm, excluding the petiole. Width — 6.3 cm. Apex — Acuminate. Base — Rounded to cordate; basal lobes are free. Aspect — Flat to slightly concave. Margins — Entire; no undulation to very slightly undulated. Texture and luster, adaxial surface — Smooth, glabrous and glossy. Texture and luster, abaxial surface — Smooth, glabrous and glossy. Juvenile and mature color, adaxial and abaxial surfaces — Variegated foliage comprised of a mixture of light red, near white base color and irregular blotches of varying size and color, from red to red-purple, greyed-orange to greyed-red, green to greyed-green, and brown. In many instances the blotches cover one half or nearly one half of the lamina, from the main vein to the margin; in other instances, the blotches occur near the base of the lamina, and, in other instances, the blotches occur in the marginal zone. In some instances, laminas are predominantly red with red-purple flecking, and nearly devoid of any blotches. The variegation pattern is variable from one leaf to the next. However, regardless of the variegation pattern and the amount of each color present, the color recitations are the same in both juvenile and mature foliage, adaxial and abaxial surfaces. The light red, near white coloration is red, nearest to RHS 36A; the mid-magenta red coloration is nearest to a blend of RHS 62A and 63B; the vibrant magenta coloration is red, nearest to a combination of RHS 50A and 52A, the light green is green to greyed-green, nearest to a blend of RHS 138A and 191A, the darker green is green, nearest to 141B and these blotches may or may not be suffused with greyed-orange to greyed-red, nearest to a combination of RHS 176A and 178A, as well as brown, RHS 200A. Venation — Pattern — Arcuate. Color, adaxial surfaces — The main vein and lateral veins are largely indistinguishable from the surrounding foliage; where veins are visible, the color is red, nearest to a combination of RHS 50A and 52A or green to greyed-green, nearest to a blend of RHS 138A and 191A. Color, abaxial surface — The main vein and lateral veins are largely indistinguishable from the surrounding foliage; where veins are visible, the color is red, nearest to a combination of RHS 50A and 52A or green to greyed-green, nearest to a blend of RHS 138A and 191A.

*Petiole*.—Attitude — Upright and outward. Aspect — Subterete. Length — 5.6 cm. Width — 0.4 cm, at the base, excluding the petiole wings. Texture and luster, adaxial surface — Smooth, glabrous and glossy. Texture and luster, abaxial surface — Smooth, glabrous and glossy. Juvenile and mature color, adaxial and abaxial surfaces — Red-purple nearest to a blend of RHS 58B and 58C, with irregular longitudinal striping colored red-purple, RHS 61C, with darker red-purple suffusion, nearest to RHS 59A.

*Petiole wings*.—Position — Proximal end of the petiole. Length — 2.8 cm. Width — 1.6 cm. Color, adaxial and abaxial surfaces — Red-purple nearest to a blend of RHS 58B and 58C, with irregular longitudinal striping colored red-purple, RHS 61C, with darker red-purple suffusion, nearest to RHS 59A.

Inflorescence: No flowering has been observed to date.

Flower buds: No flowering has been observed to date.

Flowers: No flowering has been observed to date.

Reproductive organs: No flowering has been observed to date.

Seed and fruit: No flowering has been observed to date.

COMPARISONS WITH THE PARENT PLANT

Plants of the new cultivar 'BVCL01' differ from the seed parent, *Philodendron* 'Pink Princess' (not patented), by the characteristics described in Table 1 below.

TABLE 1

| Comparison Between 'BVCL01' and 'Pink Princess' | | |
|---|---|---|
| Characteristic | 'BVCL01' | 'Pink Princess' |
| General coloration of the petiole. | Red-purple, generally appearing as vivid pink, with irregularly shaped dark pink striations. | Light pink with irregularly shaped green striations. |
| General coloration of the mature adaxial foliar surface. | Variegated foliage comprised of a light pink base coloration and irregular blotches of varying size and color, from magenta to dark pink, green to greyed-green, and brown. | Variegated foliage comprised of a green general base coloration, with near-white, pink flecking and blotching. |
| Leaf shape. | Thinner, more lanceolate leaves. | Broader, more elliptic leaves. |

COMPARISONS WITH CLOSEST KNOWN COMMERCIAL COMPARATOR

Plants of the new cultivar 'BVCL01' differ from the closest known comparator, *Philodendron* 'EM0003' (U.S. Plant Pat. No. 36,881), by the characteristics described in Table 2 below.

TABLE 2

| Comparison Between 'BVCL01' and 'EM0003' | | |
|---|---|---|
| Characteristic | 'BVCL01' | 'EM0003' |
| General coloration of the foliage. | Variegated foliage comprised of a light pink base coloration and irregular blotches of varying size and color, from magenta to dark pink, green to greyed-green, and brown. | Primarily dark yellow-green variegated foliage with swathes of varying size of nearly grey, yellow-green and light to dark pink-purple. |
| Leaf size. | Smaller than 'EM0003'; 12.5 cm in length and 6.3 cm in width, on average. | Larger than 'BVCL01'; 13.5 cm in length and 7.5 cm in width, on average. |
| Plant size of a mature specimen. | Smaller than 'EM0003'; 13.2 cm in height and 25.0 cm in width on average. | Larger than 'BVCL01'; 18.0 cm in height and 46.5 cm in width on average. |

That which is claimed is:

1. A new and distinct variety of *Philodendron* plant named 'BVCL01', substantially as described and illustrated herein.

* * * * *